United States Patent
Kim et al.

[11] Patent Number: 5,980,572
[45] Date of Patent: Nov. 9, 1999

[54] ARTIFICIAL SPINES

[75] Inventors: Phyo Kim, 15-23, Kitami 8-chome Setagaya-ku; Noriyuki Sugimoto, both of Tokyo; Masao Suzuki, Saitama-ken, all of Japan

[73] Assignees: Asahi Kogaku Kogyo Kabushiki Kaisha; Phyo Kim, both of Tokyo, Japan

[21] Appl. No.: 09/059,423

[22] Filed: Apr. 14, 1998

[30] Foreign Application Priority Data

Apr. 15, 1997 [JP] Japan ................................ 9-097117

[51] Int. Cl.⁶ .............................................. A61F 2/44
[52] U.S. Cl. .............................................. 623/17; 606/61
[58] Field of Search ........................ 623/17, 16; 606/60, 606/61

[56] References Cited

U.S. PATENT DOCUMENTS

| | | |
|---|---|---|
| 4,949,378 | 8/1990 | Hirayama et al. . |
| 4,969,913 | 11/1990 | Ojima . |
| 5,064,436 | 11/1991 | Ogiso et al. . |
| 5,147,361 | 9/1992 | Ojima et al. . |
| 5,425,772 | 6/1995 | Brantigan ................................ 623/17 |
| 5,534,031 | 7/1996 | Matsuzaki et al. . |
| 5,645,596 | 7/1997 | Kim et al. . |
| 5,728,159 | 3/1998 | Stroever et al. ........................... 623/16 |
| 5,766,252 | 6/1998 | Henry et al. .............................. 623/17 |

FOREIGN PATENT DOCUMENTS

| | | | |
|---|---|---|---|
| 2004218-C1 | 12/1993 | Russian Federation | ................. 623/17 |
| 1107-854 | 8/1984 | U.S.S.R. | ................................... 623/17 |

*Primary Examiner*—David H. Willse
*Assistant Examiner*—Suzette J. Jackson
*Attorney, Agent, or Firm*—Greenblum & Bernstein P.L.C.

[57] ABSTRACT

An artificial spine for use in an expansion of a vertebral canal which comprises an intermediate section having a pair of contacting surfaces in both ends thereof, the contacting surfaces being disposed along each outer end of a pair of divided spines; an inner side section extending from the intermediate section to between said pair of divided spines and having a width, in a horizontal cross-section thereof, which is gradually reduced in the direction of the vertebral canal; and an outer side section extending from the intermediate section to a side opposed to said inner side section, the outer side section being disposed out of the divided spaces; and at least a surface portion of the artificial spine being formed from a biocompatible ceramic material. The artificial spine has an excellent compatibility with the divided spines, and can be easily fixed to the divided spines, without hindering movement of a cervical spine.

7 Claims, 3 Drawing Sheets

ARTIFICIAL SPINES

BACKGROUND OF THE INVENTION

1. Field of the Invention

The present invention relates to an artificial spine, more particularly, an artificial spine for use in a vertebral canal expansion operation. After a spine including a vertebral arch of the cervical spine is longitudinally divided in its middle line into two parts, the artificial spine is inserted into and fixed between the divided parts of the spine.

2. Description of the Related Art

Hitherto, to remove defects caused due to the pressurizing of a spinal cord in a spondylotic myelopathy and an ossification of posterior longitudinal ligament of the cervical spine, a vertebral canal expansion operation has been carried out, and particularly a spinal longitudinal separation has been frequently carried out and now is an established operation method. In the prior art of spinal longitudinal separation, a fragmental bone is separated from an ilium, and is inserted and fixed between the longitudinally divided spines, however, such separation of the ilium is a hard on the patient.

Recently, an artificial spine of the ceramic material has been used in place of the fragmental iliac bone. However, artificial spines of the ceramic material of the prior art have a configuration which does not conform with the actual shape of the divided spines very well, and therefore they can not be fitted with a good compatibility to a gap formed between the divided spines. As a result, there arises problems of bone resorption being generated and that the adjacent artificial spines can be contacted with each other, thereby inhibiting a movement of the cervical spine.

SUMMARY OF THE INVENTION

The object of the present invention is to solve the above-mentioned problems of the prior art, and thus provide an artificial spine which has an excellent compatibility with the divided spines and enables its easy fixation of the divided spines, and which does not prevent a movement of the cervical spine.

According to the present invention, the above object can be accomplished by an artificial spine which is inserted into between a pair of longitudinally divided spines to thereby expand a vertebral canal. The artificial spine of the present invention constitutes an intermediate section having a pair of contacting surfaces on both ends thereof, the contacting surfaces being designed to be disposed along each outer end of said pair of divided spines; an inner side section extending from said intermediate section to between said pair of divided spines and having a width, in a horizontal cross-section thereof, which is gradually reduced in the direction of the vertebral canal; and an outer side section extending from said intermediate section to a side opposed to said inner side section, said outer side section being designed to be disposed out of said divided spines; and at least a surface portion of said artificial spine being formed from a biocompatible ceramic material.

The artificial spine provided according to the present invention, when it is used as a spinal spacer in an expansion operation of a vertebral canal of the cervical spine, can exhibit a remarkably improved conformability to a gap formed between the longitudinally divided spines and an excellent compatibility with the divided spines, thereby ensuring an easy fixation of the same to the divided spines, and does not inhibit movement of the cervical spine.

The present disclosure relates to subject matter contained in Japanese Patent Application No.09-97117 (filed on Apr. 15, 1997) which is expressly incorporated herein by reference in its entirety.

BRIEF DESCRIPTION OF THE DRAWINGS

The present invention will be more clearly understood from the description as set forth below with reference to the accompanying drawings, wherein.

DESCRIPTION OF THE PREFERRED EMBODIMENTS

Figure 1:
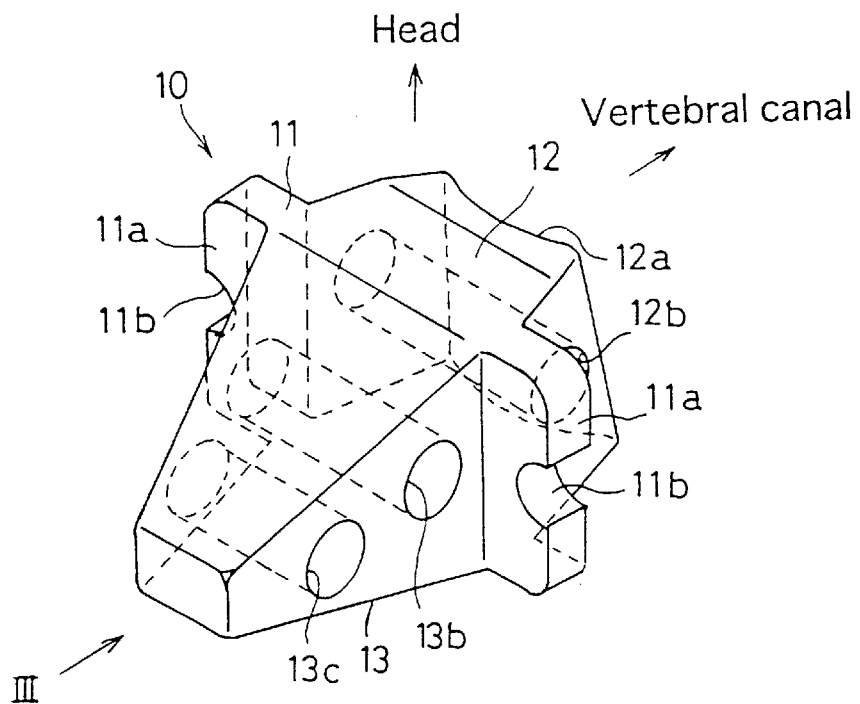
FIG. 1 is a perspective view showing one preferred embodiment of the artificial spine according of the present invention.

In the artificial spine according to the present invention, it is preferable that the inner side section and outer side section each have formed therein a thread insertion through-hole for inserting a thread for the fixation of the artificial spine to the divided spines. Further, it is desired that the ends of a pair of contacting surfaces of the intermediate section each have formed therein a thread insertion groove for guiding a thread for the fixation of the artificial spine to the divided spines.

Further, it is desired that in addition to the thread insertion through-hole, the outer side section has formed therein, a hole for facilitating bonding of the artificial spine to a surrounding tissue. Moreover, it is desired that the outer side section, in a horizontal cross-section thereof, has a configuration of a trapezoid in which its width is gradually reduced with an increase of a distance from the intermediate section, and, in a cross-section of the forehead portion, has a configuration of a trapezoid in which its upper surface accesses to its lower surface with an increase of distance from the intermediate section.

Furthermore, it is preferred that an end surface of the inner side section at one side of the vertebral canal constitutes a part of a cylindrical inner surface of the section which surface accesses and declines to one side of the intermediate side section in the direction of a head.

In the practice of the present invention, it is preferred that the biocompatible ceramic material used in the formation of the artificial spine is a glass ceramics or a calcium phosphate compound having a Ca/P ratio in the range of about 1.0 to 2.0. The calcium phosphate compound having a Ca/P ratio of about 1.0 to 2.0 usable in the present invention includes a wide variety of apatites such as hydroxyapatite, fluoroapatite and the like, monobasic calcium phosphate, dibasic calcium phosphate, tricalcium phosphate, tetracalcium phosphate, and others. These calcium phosphate compounds may be used alone or as a mixture of two or more compounds.

The calcium phosphate compounds may be produced in accordance with any well-known production methods including a wet synthesis process, a dry synthesis process and others. For example, they may be produced by drying a slurry of the starting calcium phosphate compound, followed by calcinating the dried product at a temperature of about 500 to 800° C. and then sintering at a temperature of about 800 to 1,400° C. After sintering, the resulting blocked body is fabricated to obtain a desired shape and size. Alternatively, they may be produced from powders of the above-described calcium phosphate compound by preparing a pressed powder body having a desired shape and size, followed by sintering the powder body as in the above sintering process.

In the artificial spine of the present invention, if at least a surface portion of the spine is formed from a porous ceramic material having a good biocompatibility, since the ceramic material has a good affinity with a surrounding bone tissue, a bone union can be accelerated as a function of the permeation of the bone tissue into pores of the ceramic material. The porous ceramic material used herein is preferably those having open pores. In a porous ceramic material, its pore size or diameter and its porosity are not particularly restricted, however, generally, it is preferred that the pore size is in the range of about 2 to 2,000 μm, and the porosity is in the range of about 30 to 80%, more preferably about 40 to 70%.

A core portion of the artificial spine may be formed from a dense or porous ceramic material. Usable ceramic material includes a calcium phosphate compound having a Ca/P ratio in the range of about 1.0 to 2.0, alumina, titania, zirconia, and the like. Among these materials, the calcium phosphate compound can be suitably used. When a layer of the porous biocompatible material is intended to be applied over a surface of the core portion consisting of a dense ceramic material, the method for applying the porous layer is not particularly restricted, and accordingly any conventional methods may be used in the formation of such porous layer. Suitable methods include, for example, flame spraying, sputtering, impregnation, spray coating, and the like.

The artificial spine of the present invention can satisfy its requirements, if at least a surface portion of the spine is made from a biocompatible and porous ceramic material as described above, however, it is preferred that the artificial spine is made, as a whole, from a porous ceramic material having biocompatibility.

The artificial spine according to the present invention will be further described with reference to the accompanying drawings.

Figure 4:
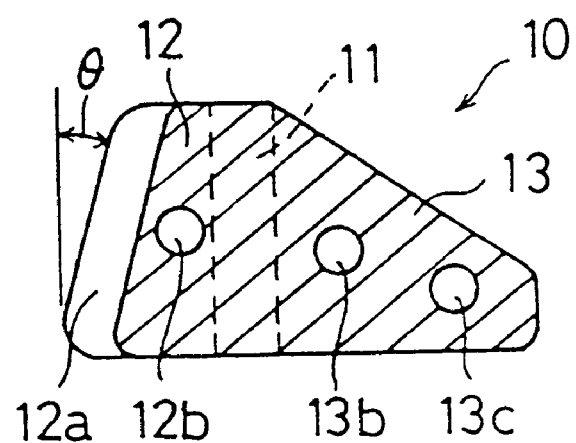
FIG. 4 is a cross-sectional view of the artificial spine of FIG. 1 taken along line IV—IV of FIG. 2.
Figure 5:
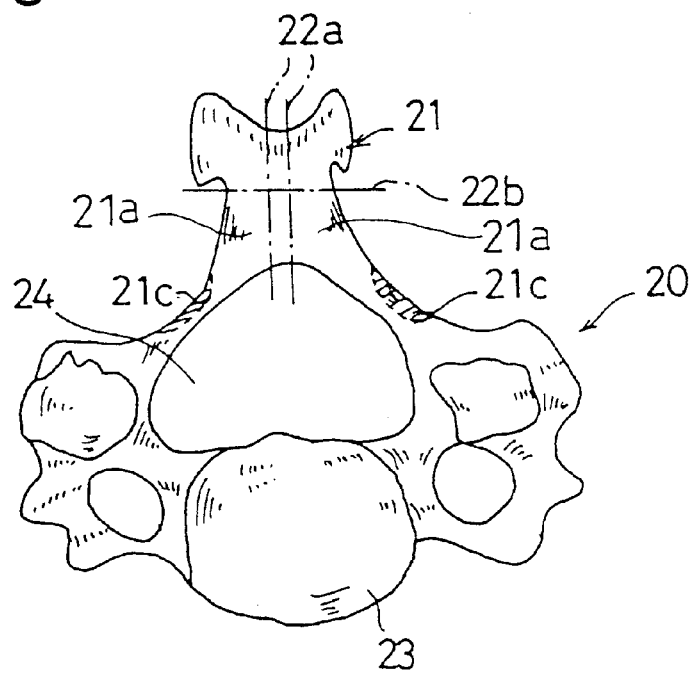
FIG. 5 is a horizontal cross-sectional view illustrating a spinal longitudinal separation of the cervical spine.
Figure 6:
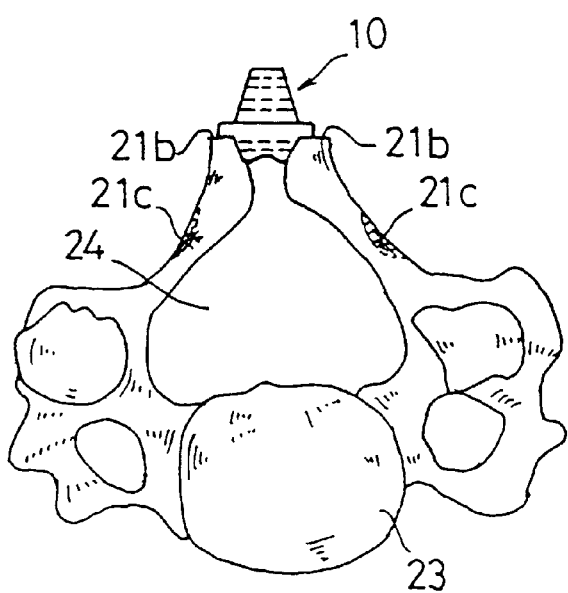
FIG. 6 is a horizontal cross-sectional view illustrating insertion of the artificial spine of the present invention into a gap of the spine, after the spine was divided and opened in accordance with the spinal longitudinal separation of FIG. 5.

In the drawings, FIGS. 1 to 4 illustrate one working example of the artificial spine 10 of the present invention, and FIGS. 5 and 6 illustrate an expansion operation of the vertebral canal in which the operation is carried out by dividing the cervical spine, and insertion of the artificial spine 10 of the present invention in a gap of the divided spines, respectively. For the spinal longitudinal separation using the artificial spine 10 of the present invention, as is illustrated in FIG. 5, a spine 21 of the cervical spine (the fourth cervical spine is illustrated) 20 is longitudinally divided in its middle line along the cutting lines 22a, and at the same time, a tip portion of the same spine 21 is cut in and removed from the cutting lines 22b. The expansion operation of the vertebral canal is carried out by bending the resulting divided spines 21a into right and left directions (right and left of FIGS. 5 and 6). The reference numerals 23 and 24 represent a centrum of vertebrae and a vertebral canal, respectively.

As is illustrated in FIGS. 1 to 4, the artificial spine 10 of the present invention is constituted from an intermediate section 11, an inner side section 12 and an outer side section 13. The intermediate section 11 has a pair of contacting surfaces 11a in both ends thereof. In use of the artificial spine 10, the contacting surfaces 11a can be disposed along the outer end 21b of the divided spines 21a obtained upon the cutting of the spine 10.

Figure 2:
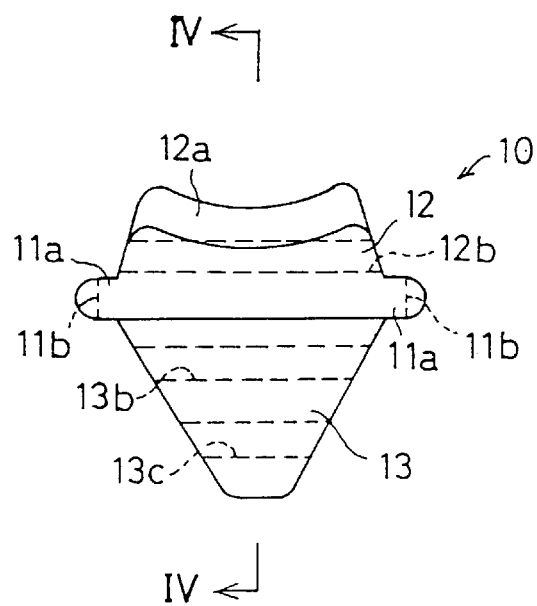
FIG. 2 is a plane view of the artificial spine of FIG. 1.
Figure 3:
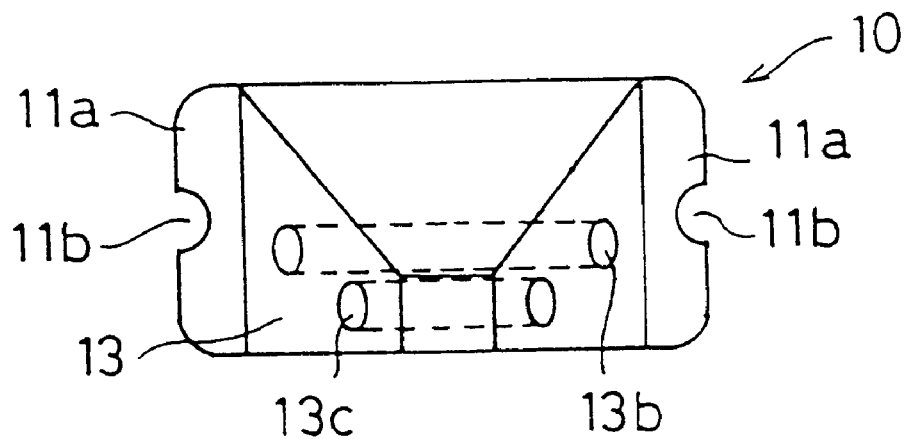
FIG. 3 is a front view of the artificial spine of FIG. 1 taken in the direction of the arrow III.

The inner side section 12 has a configuration capable of extending from a central portion of the intermediate section 11 to a space formed between a pair of the divided spines 21a. In a horizontal cross-section thereof, the inner side section 12 has a width which is gradually reduced in the direction of the vertebral canal 24. Further, in this inner side section 12, its end surface positioning at a side (inner side) of the vertebral canal 24 constitutes a part of a cylindrical inner surface 12a of the same section 12, and, as is illustrated in FIGS. 2 and 4, the cylindrical inner surface 12a is declining to the intermediate side section 11 in the direction of a head. A curved surface of the cylindrical inner surface 12a is provided so that it can satisfy the requirement concerning a height of a spinal cord-dural canal which will be received and positioned in the inner surface 12a, and an anlge θ (see, FIG. 4) is provided so that it can be conformed to an angle of the side edge of the divided spines 21a, thereby ensuring a parallel maintenance of the cylindrical inner surface 12a of the artificial spine 10 to the spinal cord-dural canal.

The outer side section 13 has a configuration capable of extending from a central portion of the intermediate section 11 to a direction which is opposite to a pair of the divided spines 21a. As in the above-described inner side section 12, in a horizontal cross-section thereof, the outer side section 13 has a width which is gradually reduced in the direction of its tip portion. Further, the outer side section 13 has an upper surface which is gradually declining in the direction of its lower surface, and, in a cross-section of the forehead portion (perpendicular cross-section), has a configuration of a trapezoid. The configuration of this outer side section 13 is similar to that of a real spine, and thus it is expected that the artificial spine of the present invention can effectively act in the adhesion and reconstruction of muscles.

In each of the inner side section 12 and the outer side section 13, there is a thread insertion through-hole 12b and 13b for inserting a fixation thread such as nylon wire for fixing the artificial spine 10 to the divided spines 21a formed therein, respectively, and, in the intermediate section 11, there is a thread insertion (and fixation) groove 11b formed in each of the ends of the pair of contacting surfaces 11a. In addition, in the outer side section 13, there is a bonding-facilitating hole 13c for facilitating the bonding of the artificial spine 10 to a surrounding tissue (paravertebral muscles).

The artificial spine 10 having the above-described structure is inserted into and fixed to between a pair of divided spines 21a in such a manner that the inner side section 12 is directed to a side of the vertebral canal 24 and the outer side section 13, in its cross-section of the forehead portion, has a lower and flat surface directed to a side of the legs. In this insertion of the artificial spine 10, it is preferred that removable portion 21c is shaped and removed from a base portion of the cervical spine 20 so that the pair of divided spines 21a can be easily deformed. Then, the pair of contacting surfaces 11a of the intermediate section 11 are intimately contacted to each of the outer end portion 21b of the corresponding pair of divided spines 21a, thereby stabilizing the fixed artificial spine 10, and the fixation threads are guided through the thread insertion through-hole 12b of the inner side section 12, the thread insertion groove 11b of the intermediate section 11 and the thread insertion through-hole 13b of the outer side section 13 as well as a fixation hole bored in the divided spines 21a. As a result, the artificial spine 10 is fixed to the divided spines 21a. After the operation, an adhesion of the artificial spine 10 with the surrounding muscles and reconstruction of the supporting structure can be expected as a function of the outer side section 13 and its bonding-facilitating hole 13c. Using the artificial spine 10 of the present invention, it becomes possible to construct a bonding between the spine and the proper dorsal muscles, and reconstruct a mechanical supporting structure of the cervical spine.

EXAMPLES

The present invention will be further described with reference to the production of the artificial spine of the present invention which is illustrated in FIGS. 1 to 4. Note, however, that the present invention should not be restricted to these examples.

Production Example 1

Calcinated apatite powders and methyl cellulose powders were blended in a rotary mixer. The resulting mixed powders were contained in a rubber-made mold, and a pressure of $2t/cm^2$ was applied to the powders in a hydrostatic press to obtain a dried product. The dried product was then fabricated in an NC machine, in anticipation of shrinkage of the product during sintering, to obtain a shape illustrated in the figures. The fabricated product was fired at a temperature of 1,100° C. for 2 hours in an electric oven.

Production Example 2

Calcinated apatite powders and methyl cellulose powders were dissolved in pure water, and thoroughly mixed. The resulting suspension was foamed in a foaming machine, and then dried for about one hour in a drying machine to obtain a dried porous product. The dried product was then fabricated in a NC machine, in anticipation of shrinkage of the product during sintering, to obtain a shape illustrated in the figures. The fabricated product was fired at a temperature of 1,200° C. for about 3 days in an electric oven.

Production Example 3

Calcinated apatite powders were subjected to a primary compression process to obtain a molded product. A pressure of $2t/cm^2$ was applied to the molded product in a hydrostatic press to obtain a dried product. The dried product was then fabricated in a NC machine, in anticipation of shrinkage of the product during sintering, to obtain a shape illustrated in the figures. The fabricated product was fired at a temperature of 1,100° C. for about 3 days in an electric oven.

What is claimed is:

1. An artificial spine, as a spacer for the spine, which is to be inserted into between a pair of longitudinally divided spines of a spinous process to thereby expand a vertebral canal, said artificial spine comprising:

an intermediate section having a pair of contacting surfaces in both ends thereof, said contacting surfaces being designed to be disposed along each outer end of said pair of divided spines;

an inner side section extending from said intermediate section to between said pair of divided spines and having a width, in a horizontal cross-section thereof, which is gradually reduced in the direction of said vertebral canal; and an outer side section extending from said intermediate section to a side opposed to said inner side section, said outer side section being designed to be disposed out of said divided spines; and, wherein at least one surface portion of said artificial spine being formed from a biocompatible ceramic material.

2. An artificial spine as defined in claim 1, in which said inner side section and said outer side section each have formed therein a thread insertion through-hole for inserting a thread for use in the fixation of said artificial spine to said divided spines.

3. An artificial spine as defined in claim 2, in which in addition to said thread insertion through-hole, said outer side section further has a hole for accelerating bonding of said artificial spine to a surrounding tissue.

4. An artificial spine as defined in claim 1 in which each of the ends of said pair of contacting surfaces of said intermediate section have formed therein a thread insertion groove for guiding a thread for use in the fixation of said artificial spine to said divided spines.

5. An artificial spine as defined in claim 1 in which an end surface of said inner side section at a side of said vertebral canal constitutes a part of a cylindrical inner surface of said section which surface accesses and declines to a side of said intermediate side section in the direction of a head.

6. An artificial spine as defined in claim 1 in which said outer side section, in a horizontal cross-section thereof, has a configuration of a trapezoid and a width of said trapezoid is gradually reduced with an increase of a distance from said intermediate section.

7. An artificial spine as defined in claim 1 in which said outer side section, in a cross-section of the forehead portion, has a configuration of a trapezoid and an upper surface of said trapezoid accesses to its lower surface with an increase of distance from said intermediate section.

* * * * *